United States Patent [19]

Blaszczak et al.

[11] Patent Number: 4,492,694
[45] Date of Patent: Jan. 8, 1985

[54] INDOLYLGLYCYL CEPHALOSPORIN DERIVATIVES

[75] Inventors: Larry C. Blaszczak, Indianapolis; Jan R. Turner, Carmel, both of Ind.

[73] Assignee: Eli Lilly and Company, Indianapolis, Ind.

[21] Appl. No.: 484,340

[22] Filed: Apr. 12, 1983

[51] Int. Cl.³ .................... A61K 31/545; C07D 501/22
[52] U.S. Cl. ...................................... 424/246; 544/21; 544/22; 544/28; 548/507
[58] Field of Search .................. 424/246; 544/22, 28, 544/21

[56] References Cited

U.S. PATENT DOCUMENTS

| | | | |
|---|---|---|---|
| 3,364,212 | 1/1968 | Patchett | 544/28 |
| 3,518,260 | 6/1970 | Spencer et al. | 544/30 |
| 3,560,489 | 2/1971 | Morin | 544/28 |
| 4,024,137 | 5/1977 | Cook et al. | 544/28 |

*Primary Examiner*—Paul M. Coughlan, Jr.
*Attorney, Agent, or Firm*—Charles W. Ashbrook; Arthur R. Whale

[57] ABSTRACT

7-(3-Indolyl)glycylamido cephalosporins have good gram positive activity and favorable pharmacokinetics and are orally effective.

40 Claims, No Drawings

INDOLYLGLYCYL CEPHALOSPORIN DERIVATIVES

BACKGROUND OF THE INVENTION

The cephalosporin class of antibiotics has been extensively studied, and several members of the class are now routinely used to combat bacterial diseases caused by a broad spectrum of gram positive and gram negative microorganisms. The majority of such compounds are not effective orally, but rather are administered intramuscularly or intravenously, thus necessitating assistance from medically trained personnel. Moreover, since the compounds are effective against a broad spectrum of microorganisms, they generally are not employed for their specificity.

There remains a need for cepahlosporin antibiotics that are orally effective and have a degree of specificity toward one or more groups of microorganisms. An object of this invention is to provide a group of compounds that satisfy these needs.

SUMMARY OF THE INVENTION

This invention concerns cephalosporin antibiotics. The invention is more particularly directed to a group of (3-indolyl)glycylamido cephalosporin derivatives having the formula

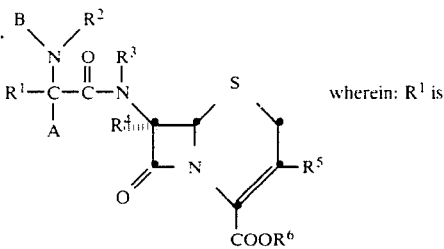

wherein: $R^1$ is

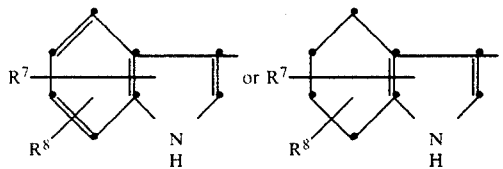

in which
$R^7$ and $R^8$ independently are hydrogen, halo, hydroxy, $C_1$-$C_4$ alkyl, $C_1$-$C_4$ alkoxy, nitro, amino, $C_1$-$C_4$ alkanoylamino, $C_1$-$C_4$ alkylsulfonylamino, or when $R^7$ and $R^8$ are on adjacent carbon atoms, they may be taken together to form methylenedioxy;

A and B both are hydrogen, or taken together complete a double bond;

$R^2$ is hydrogen, an amino protecting group, hydroxy, or methoxy, and $R^3$ is hydrogen, or $R^2$ and $R^3$ taken together are

where
M and N independently are $C_1$-$C_4$ alkyl;
$R^4$ is hydrogen, methoxy or methylthio;

$R^5$ is hydrogen, methoxy, methyl, halo, methoxymethyl, or vinyl;

$R^6$ is hydrogen, a salt forming cation group, or a carboxy protecting group; and the pharmaceutically acceptable acid addition salts thereof; with the proviso that $R^2$ is hydroxy or methoxy only when A and B complete a double bond, and that A and B both are hydrogen when $R^3$ is other than hydrogen.

Preferred compounds provided by the invention include those of the above formula wherein $R^1$ is

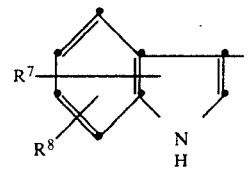

and $R^7$ and $R^8$ are as defined above. Within this group, preferred compounds include those wherein $R^2$ is hydrogen, an amino protecting group, hydroxy or methoxy, and $R^6$ is hydrogen or a carboxy protecting group.

Another preferred group of compounds are those wherein $R^1$ is

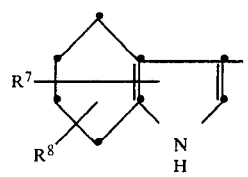

and $R^7$ and $R^8$ are as defined above. Especially preferred compounds within this group include those wherein A, B, $R^2$, $R^3$, $R^4$ and $R^6$ are hydrogen.

A particularly preferred group of compounds provided by this invention are defined by the formula

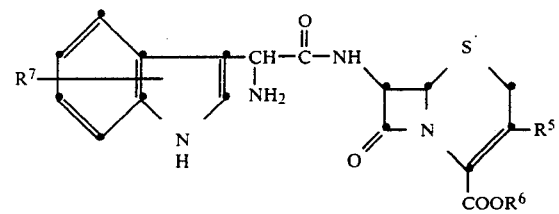

wherein $R^5$, $R^6$ and $R^7$ are as defined above. The most preferred compounds are those within this group wherein $R^7$ is hydrogen, halo, hydroxy or methoxy, $R^5$ is methyl or chloro, and $R^6$ is hydrogen or a salt forming group such as sodium or potassium cation.

An additional embodiment of this invention is a pharmaceutical formulation comprising a indolylglycylamido cephalosporin derivative as defined above admixed with a pharmaceutical carrier, diluent or excipient therefor. A preferred formulation is one suitable for oral administration.

Yet another embodiment of this invention is a method for treating bacterial infections in animals comprising administering an effective amount of an antibacterial compound of the above formula. In a preferred method of treatment, the indolylglycyl cephalosporin derivative is administered orally.

DETAILED DESCRIPTION OF THE INVENTION

In the above formulas defining the compounds provided by this invention, $R^1$ defines a 3-indolyl group of the formula

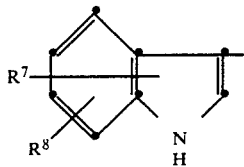

or a 3-(4,5,6,7-tetrahydroindolyl) group of the formula

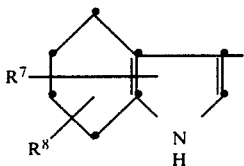

These indolyl and tetrahydroindolyl groups can be unsubstituted, for instance when $R^7$ and $R^8$ both are hydrogen; or mono-substituted, for instance when one of $R^7$ or $R^8$ is hydrogen and one is other than hydrogen; or di-substituted, for instance when $R^7$ and $R^8$ both are other than hydrogen. $R^7$ can be located at the 2-position of the bicyclic ring system, or at the 4, 5, 6 or 7 position.

$R^7$ and $R^8$ are defined above to include $C_1$-$C_4$ alkyl, $C_1$-$C_4$ alkoxy, halo, $C_1$-$C_4$ alkanoylamino and $C_1$-$C_4$ alkylsulfonylamino. The term "$C_1$-$C_4$ alkyl" carries its art-recognized meaning of straight and branched lower alkyl carbon chains such as methyl, ethyl, isopropyl, n-propyl, iso-butyl and tert.-butyl. Similarly, "$C_1$-$C_4$ alkoxy" refers to lower alkyl groups bonded to the indolyl or tetrahydroindolyl bicyclic ring through an oxygen atom. Typical $C_1$-$C_4$ alkoxy groups include methoxy, ethoxy, n-propoxy, n-butoxy and iso-butoxy. The term "halo" as used herein includes fluoro, chloro, bromo and iodo. Preferred halo groups include chloro and fluoro.

$R^7$ and $R^8$ also represent $C_1$-$C_4$ alkanoylamino and $C_1$-$C_4$ alkylsulfonylamino. Typical alkanoylamino groups include formylamino, acetylamino, and isobutyrylamino. Typical $C_1$-$C_4$ alkylsulfonylamino groups are methylsulfonylamino, ethylsulfonylamino and n-butylsulfonylamino.

$R^2$ in the above formula defines a substituent on the glycyl nitrogen atom, and includes hydrogen and an amino protecting group. The term "amino protecting group" refers to any of the art-recognized substituents that can be attached to an amino nitrogen atom and which is readily removed when desired. Such protecting groups are often employed during preparation of the compounds of the invention, and serve to improve solubility in organic solvents and to decrease the likelihood of unwanted side reactions occurring as a result of the presence of a free amino group. While the compounds wherein $R^2$ is a protecting group are expected to have biological activity, it is contemplated that the most biologically desirable compounds will be those wherein $R^2$ is hydrogen. The compounds wherein $R^2$ is an amino protecting group are thus primarily useful as intermediates in the synthesis of the more preferred free amino compounds.

The precise nature of the amino protecting group is not critical to the invention, and any of the well known protecting groups can be employed. Typical amino protecting groups are described by J. W. Barton in "Protective Groups in Organic Chemistry," J. F. McOmie, Ed., Plenum Press, New York, N.Y., 1973 Chapter 2, and by Greene in "Protective Groups in Organic Synthesis," John Wiley & Sons, New York, N.Y., 1981, Chapter 7, incorporated herein by reference for their teaching of amino protecting groups.

The most common amino protecting groups to be employed include $C_1$-$C_{10}$ alkanoyl and halo $C_1$-$C_{10}$ alkanoyl groups such as formyl, acetyl, chloroacetyl, dichloroacetyl, propionyl, hexanoyl, 3,3-diethylhexanoyl, $\gamma$-chlorobutyryl, and the like; $C_1$-$C_{10}$ alkoxycarbonyl, $C_1$-$C_{10}$ alkenyloxycarbonyl, and $C_5$-$C_{15}$ aryloxycarbonyl groups such as tert.-butoxycarbonyl, benzyloxycarbonyl, allyloxycarbonyl, 4-nitrobenzyloxycarbonyl and cinnamoyloxycarbonyl; halo-$C_1$-$C_{10}$ alkoxycarbonyl such as 2,2,2-trichloroethoxycarbonyl; and $C_1$-$C_{15}$ arylalkyl and alkenyl groups such as benzyl, phenethyl, allyl, trityl, and the like. Other commonly used amino protecting groups are those in the form of enamines prepared with $\beta$-keto-esters such as methyl or ethyl acetoacetate.

$R^2$ in the above formula, in addition to representing hydrogen or an amino protecting group, also, when taken together with $R^3$, completes a ring system to provide compounds of the formula

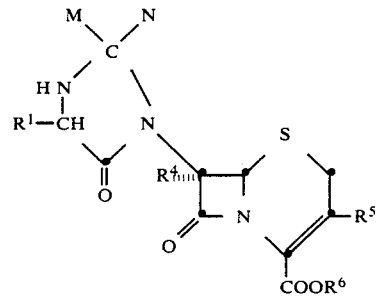

where $R^1$, $R^4$, $R^5$, $R^6$, M, and N are as defined above. Typical of these compounds are the acetonides, for example those wherein M and N both are methyl. Such compounds are particularly useful as long-acting antibacterial agents.

$R^6$ in the above formula is hydrogen; a salt forming group such as ammonium or an alkali metal cation, for example lithium, sodium or potassium; or a carboxy protecting group. The term "carboxy protecting group" refers to the art-recognized groups commonly employed to block or protect the carboxylic acid functionality of a cephalosporin molecule during chemical reactions involving other functional sites in the molecule, and which can be readily removed when desired by common hydrolytic or hydrogenolytic techniques. Typical carboxy protecting groups to be employed according to this invention include those described by E. Haslam in "Protective Groups in Organic Chemistry", supra, Chapter 5, and by Greene in "Protective Groups in Organic Synthesis", supra, Chapter 5, both of which are incorporated herein by reference. Examples of the commonly employed carboxy protecting groups include $C_1$–$C_{10}$ alkyl groups such as methyl, tert.-butyl, decyl; halo-$C_1$–$C_{10}$ alkyl such as 2,2,2-trichloroethyl, and 2-iodoethyl; $C_5$–$C_{15}$ arylalkyl such as benzyl, 4-methoxybenzyl, 4-nitrobenzyl, triphenylmethyl, diphenylmethyl; $C_1$–$C_{10}$ alkanoyloxymethyl such as acetoxymethyl, propionoxymethyl and the like; and groups such as phenacyl, 4-halophenacyl, allyl, dimethylallyl, tri($C_1$–$C_3$ alkyl)silyl such as trimethylsilyl, β-p-toluenesulfonylethyl, β-p-nitrophenylthioethyl, 2,4,6-trimethylbenzyl, β-methylthioethyl, phthalimidomethyl, 2,4-dinitrophenylsulphenyl, 2-nitrobenzhydryl and related groups.

The 3-indolylglycyl cephalosporin derivatives provided by this invention can be prepared by any of several methods. A preferred method comprises reacting a 7-aminocephalosporin nucleus with a 3-indolylglycine derivative according to the following scheme:

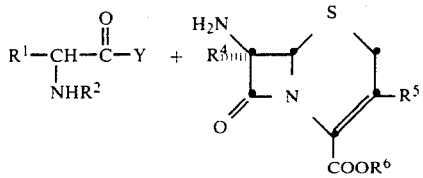

wherein $R^1$, $R^2$, $R^4$, $R^5$ and $R^6$ are as defined above, and Y is a leaving group such as hydroxy; halo, for instance chloro, bromo, or iodo; lower alkanoyloxy such as formyloxy, acetoxy or the like. Typical 3-indolylglycine derivatives commonly employed in such direct coupling reactions include those of the formula

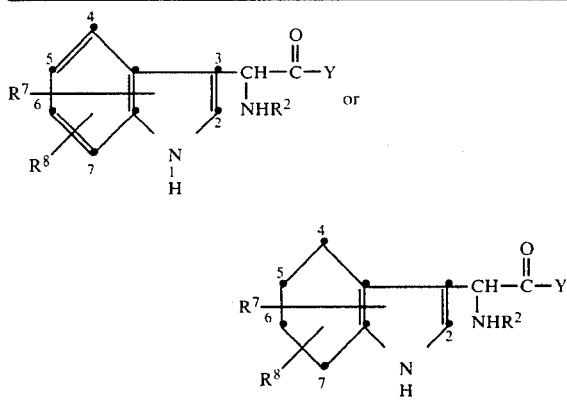

| wherein: $R^7$ | $R^8$ | $R^2$ | Y |
|---|---|---|---|
| H | H | acetyl | OH |
| H | H | chloroacetyl | Cl |
| H | H | H | Cl (as a hydrochloride) |
| H | H | formyl | OCHO |
| 5-Cl | H | p-nitrobenzyloxycarbonyl | OH |
| H | H | H | OH |
| 5-OCH$_3$ | H | H | OH |
| 6-OCH$_3$ | 4-Cl | tert.-butoxycarbonyl | Cl |
| 2-OCH$_3$ | 5-Br | benzyl | Br |
| 7-OCH$_2$CH$_3$ | H | trimethylsilyl | OCHO |
| 4-OCH$_3$ | 5-OCH$_3$ | p-nitrobenzyl | OCOCH$_3$ |
| 2-Cl | 6-NO$_2$ | H | OH |
| 2-Br | 6-NH$_2$ | benzyloxycarbonyl | Br |
| 4-F | H | tert.-butoxycarbonyl | Cl |
| 7-Cl | H | H | Br (hydrobromide) |
| 7-I | 4-acetylamine | 2,2,2-trichloroethoxycarbonyl | Cl |
| 4-CH$_3$ | H | H | OH |
| 2-CH$_3$ | 5-CH$_2$CH$_3$ | formyl | Cl |
| 7-CH$_2$CH$_3$ | H | acetyl | OH |
| 5-CH$_2$CH$_2$CH$_3$ | 6-F | benzoyl | HCHO |
| H | 6-methylsulfonylamino | H | Cl (hydrochloride) |
| H | 5-Cl | allyloxycarbonyl | OCOCH$_3$ |

The indolylglycine derivatives thus described are either known commercially or are available by methods generally familiar to those skilled in the art of organic chemistry. For example, British Pat. No. 1,399,089 describes the synthesis of indolylglyoxylic acids and oximes, the latter being readily convertible to indolylglycines. U.S. Pat. No. 3,976,680 describes a method for preparing optically pure indolylglycines.

Like the indolylglycine starting materials, the cephalosporin nuclei required for the synthesis of the present compounds are readily available or can be prepared by methods well known in the art. For example, the 3-halo cephalosporin nuclei can be prepared by the methods taught in U.S. Pat. No. 3,925,372. 3-Methyl cephalosporins are available by ring expansion of penicillin sulfoxides and subsequent side chain cleavage. The 3-vinyl cephem nucleus is available by the method of U.S. Pat. No. 3,994,884.

Typical cephalosporin nuclei that will be employed in the synthesis of compounds of the present invention are illustrated below:

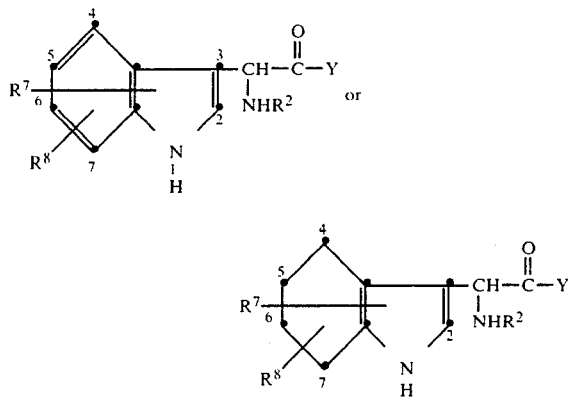

| $R^4$ | $R^5$ | $R^6$ |
|---|---|---|
| H | CH$_3$ | H |
| H | CH$_3$ | tert.-butyl |
| H | Cl | p-nitrobenzyl |
| CH$_3$O | H | methyl |
| CH$_3$S | CH$_3$ | H |
| H | —CH$_2$OCH$_3$ | 2,2,2-trichloroethyl |
| H | —CH=CH$_2$ | benzyl |

-continued

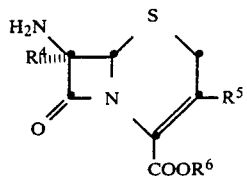

| R[4] | R[5] | R[6] |
|---|---|---|
| H | OCH3 | allyl |
| CH3O | Br | H |
| CH3S | H | tert.-butyl |
| H | I | Na |

The coupling of a 3-indolyllglycine or tetrahydroindolylglycine derivative with a 7-aminocephalosporin nucleus can be accomplished employing common techniques of acylation. For example, a indolylglycyl acylating agent, wherein Y in the above formula is a leaving group such as halo, especially chloro or bromo, or alkanoyloxy such as formyloxy or acetoxy, can be reacted with a cephalosporin nucleus employing standard acylation conditions. During such acylation reaction, it generally is preferred that R[2] in the above formula be an amino protecting group and that R[6] be a carboxy protecting group. These protecting groups serve to minimize unwanted side reactions and to increase solubility characteristics of the respective reactants.

The acylation reaction generally is accomplished by combining approximately equimolar quantities of a 3-indolylglycyl acylating agent (i.e. an acid halide or mixed acid anhydride) with the 7-aminocephalosporin nucleus. The acylation reaction normally is carried out in a mutual solvent such as benzene, chloroform, dichloromethane, toluene, N,N-dimethylformamide, acetonitrile, or the like, and routinely is substantially complete after about 1 to about 12 hours when conducted at a temperature of about $-20°$ to about $60°$ C. About an equimolar quantity of a base such as pyridine, triethylamine, aniline, sodium carbonate or the like, can be employed in the reaction if desired to act as an acid scavenger. The product may be isolated from the reaction mixture by simply removing the reaction solvent, for instance by evaporation under reduced pressure, and further purification can be accomplished if needed employing routine techniques such as chromatography, crystallization, solvent extraction, and related methods.

An alternative and preferred method for coupling an indolylglycine derivative to a 7-aminocephalosporin nucleus to produce compounds of the invention employs a coupling reagent such as those routinely used in the synthesis of peptides. Typical coupling reagents that can be employed include carbodiimides such as N,N'-diethylcarbodiimide, N,N'-diisopropylcarbodiimide, and N,N'-dicyclohexylcarbodiimide (DCC); carbonyl coupling reagents such as carbonyldiimidazole; isoxazolinium salts such as N-ethyl-5'-phenylisoxazolinium-3'-sulfonate; and quinoline compounds such as N-ethoxycarbonyl-2-ethoxy-1,2-dihydroquinoline (EEDQ).

The coupling of a 7-aminocephalosporin nucleus with a indolylglycine derivative employing a peptide coupling reagent generally is accomplished by combining approximately equimolar quantities of a 7-aminoceph-3-em-4-carboxylic acid, in indolylglycine, and a peptide coupling reagent according to the following scheme;

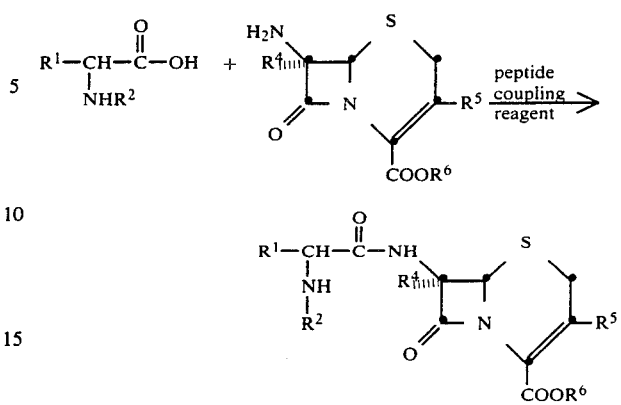

wherein $R^1$, $R^2$, $R^4$, $R^5$ and $R^6$ are as defined above. Preferably $R^2$ is an amino protecting group and $R^6$ is hydrogen or a carboxy protecting group during such coupling reactions. Any such protecting groups can be subsequently removed by standard methods to give the active antibiotic of the invention.

The coupling reaction normally is conducted in a mutual solvent such as dichloromethane, acetone, water, acetonitrile, N,N-dimethylformamide, chloroform, or the like, and routinely is substantially complete when carried out for about ten to about ninety minutes at a temperature of about $-20°$ to about $60°$ C. Longer reaction periods are not detrimental to the product and can be employed if desired. The product, an indolylglycyl cephalosporin derivative of the invention, is readily isolated by simply removing the reaction solvent, for instance by evaporation under reduced pressure. The product can be purified if needed by standard methods such as acid-base extraction, chromatrography, salt formation or the like.

Still another method for preparing compounds of the invention employs an indolyl oxime derivative of the formula

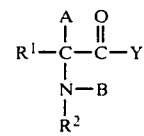

wherein $R^1$ and Y have the above-defined meanings, A and B are taken together to form a bond, and $R^2$ is hydroxy or methoxy. When $R^2$ is hydroxy, it generally is protected with trimethylsilyl or similar hydroxy protecting group. Such indolyl oxime derivatives can be coupled to a cephalosporin nucleus by any of the methods described above to provide a compound of the formula

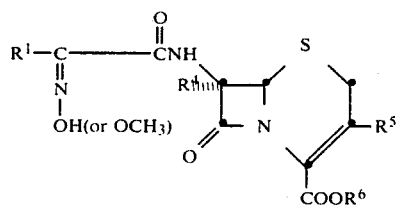

wherein $R^1$, $R^4$, $R^5$, and $R^6$ are as defined above. These compounds are useful as intermediates since they are readily reduced by normal methods to give the preferred indolylglycyl compounds of the invention. Additionally, the oximes of the above formula wherein $R^6$ is hydrogen or a salt forming group are potent antibiotics.

Yet another alternative method for preparing compounds of the invention comprises chemically modifying a position on an intact indolylglycyl cephalosporin. For example, a 3-exomethylene cephalosporin nucleus can be acylated with a indolylglycyl derivative to form an indolylglycyl 3-exomethylene cephalosporin. The latter compound can be converted by known methods to compounds of the invention. For instance, ozonolysis of an indolylglycyl 3-exomethylene cephalosporin affords a 3-hydroxy compound. Halogenation of a 3-hydroxy compound affords the 3-halo indolylglycyl cephalosporins of the invention, while reaction with a base and a methylating agent affords the 3-methoxy compounds of the invention.

Compounds of the invention that bear a nitro group on the indolyglycyl or the tetrahydroindolylglycyl side chain can be modified to provide other compounds of the invention. For example, the nitro substituent can be reduced by routine reduction or hydrogenation procedures to give the corresponding amino substituted indolyglycyl cephalosporin derivative, which if desired can be acylated by reaction with a $C_1$-$C_4$ alkanoyl halide or anhydride or a $C_1$-$C_4$ alkylsulfonyl halide to provide the corresponding alkanoylamino or alkylsulfonylamino indolylglycylamido cephalosporin of the invention.

Similarly, compounds of the invention wherein $R^2$ and $R^3$ are taken together to form the group

are prepared by reacting a ketone of the formula

with a compound of the invention wherein $R^2$ and $R^3$ both are hydrogen, generally in the presence of an acid such as methanesulfonic acid or the like. The cyclic compounds thus produced, for instance the preferred acetonides wherein M and N both are methyl, are particularly useful as oral antibiotics since they are effective over prolonged periods of time.

Other compounds of the invention that are expected to be particularly long acting antibiotics are those wherein $R^2$ is an alkanoyl amino protecting group such as formyl or acetyl. Such compounds are conveniently prepared by simply reacting an indolylglycylamido cephalosporin, wherein $R^2$ is hydrogen, with a $C_1$-$C_{10}$ alkanoyl acylating agent, for instance formyl chloride or acetic anhydride. These N-acylated products are expected to act not only as antibiotics in themselves, but also as pro-drugs in that they will be hydrolyzed in an animal system to the parent indolylglycyl derivative.

It should be noted that since the indolylglycyl side chains of the cephalosporins of this invention contain one asymmetric carbon atom, for example when A is hydrogen, the compounds of the invention can exist in the form of optical isomers, namely the D and the L isomers. The compounds of the invention can be employed as a DL-mixture to treat bacterial infections in animals, or if desired the optical isomers can be separated and employed individually. While both isomers are effective antibacterial agents, one isomer appears to be more potent than the other and is designated herein as the D-isomer, and accordingly is a preferred embodiment of the invention.

Separation or resolution of the optical isomers can be accomplished by routine methods carried out on the cephalosporin product of the invention or on the indolylglycine side chain that is employed as a starting material. Separation of optical isomers generally will be accomplished by high performance chromatography, enzymatic resolution, or chemical crystallization or resolution. A particularly preferred method for obtaining D-(3-indolyl)glycines comprises reacting the D,L-mixture with benzaldehyde and optically active tartaric acid according to the method of U.S. Pat. No. 3,976,680.

As noted above, preferred compounds of the invention are those wherein $R^2$ in the above formula is hydrogen. Such compounds, being primary amines, are basic in nature and readily form pharmaceutically acceptable salts by reaction with acids. Typical acids commonly employed to form salts include inorganic acids such as hydrogen chloride, hydrogen bromide, sulfuric acid, phosphoric acid; as well as organic acids such as acetic acid, trifluoroacetic acid, succinic acid, methanesulfonic acid, oxalic acid, para-toluenesulfonic acid, and the like. The compounds of the invention wherein both $R^2$ and $R^6$ are hydrogen readily form an internal acid addition salt, namely a zwitterion. The compounds of the invention generally exist as crystalline solids and can be crystallized from common solvents such as acetone, ethanol, N,N-dimethylformamide, water or the like. The components often form solvates or hydrates and can be employed in such forms according to the invention.

Examples of typical classes of indolylglycyl cephalosporins, as well as specific compounds provided by this invention, include those listed below:

Preferred Compounds of the formula

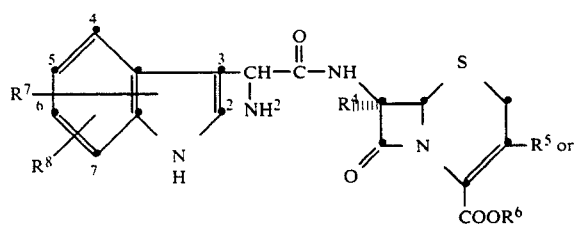

-continued

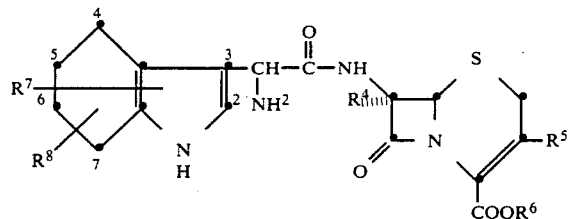

| R⁷ | R⁸ | R⁴ | R⁵ | R⁶ |
|---|---|---|---|---|
| H | H | H | $CH_3$ | H |
| H | H | H | Cl | H |
| H | H | H | $CH=CH_2$ | H |
| H | 4-Cl | H | H | $Na^+$ |
| 2-OH | H | $CH_3O-$ | $CH_2OCH_3$ | H |
| 4-Br | 7-$CH_3$ | H | $OCH_3$ | H |
| 2-$CH_3$ | 6-$OCH_2CH_3$ | $CH_3S-$ | Br | $NH_4^+$ |
| 5-F | 6-F | H | $CH_3$ | H |
| H | 6-$NO_2$ | H | $CH_3$ | $K^+$ |
| H | 6-$NH_2$ | H | $CH_3$ | H |
| H | 6-$NHCOCH_3$ | $CH_3O-$ | F | H |
| 5,6-methylene-dioxy | | H | $CH_3$ | H |
| 5-OH | H | H | $CH_3$ | H |
| 6-OH | H | H | $CH_3$ | H |
| 2-Cl | 6-$NHSO_2CH_2CH_3$ | H | $CH=CH_2$ | H |
| 5-$OCH_2CH(CH_3)_2$ | H | H | H | tert-butyl |
| 6-OH | 7-$CH_3$ | $CH_3S-$ | $CH_2OCH_3$ | p-nitrobenzyl |
| H | H | H | $CH_3$ | $CH_2CH=CH_2$ |
| H | H | H | Cl | $CH_2CCl_3$ (hydrochloride) |
| 6-Cl | H | H | $OCH_3$ | trimethylsilyl |
| 2-$CH_3$ | H | H | $CH_3$ | H |

Compounds of the formula

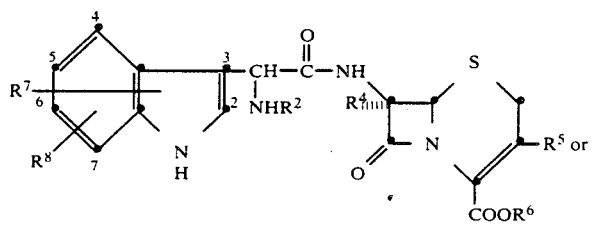

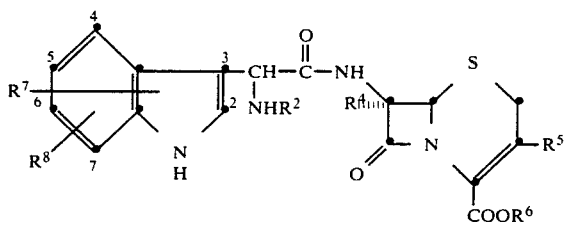

| R⁷ | R⁸ | R² | R⁴ | R⁵ | R⁶ |
|---|---|---|---|---|---|
| H | H | COOtert.butyl | H | $CH_3$ | H |
| H | H | $COOCH_2CH=CH_2$ | H | Cl | H |
| H | 6-$OCH_3$ | $COCH_3$ | $CH_3O$ | H | H |
| 2-Cl | 6-$OCH_3$ | $COOCH_2CCl_3$ | H | $OCH_3$ | $CH_2CCl_3$ |
| 4-$CH_3$ | H | $CH_2\phi$ | H | $CH_2OCH_3$ | p-nitrobenzyl |
| 5-Br | 6-Br | $C(\phi)_3$ | $CH_3S$ | Br | $CH_3$ |
| H | 6-OH | CHO | H | $CH=CH_2$ | $CH_2OCOCH_3$ |
| H | H | OH | H | $CH_3$ | H |
| H | H | $OCH_3$ | H | Cl | H |
| H | H | OH | $CH_3O$ | $CH_2OCH_3$ | H |
| H | H | $OCH_3$ | H | H | tert.-butyl |
| H | 6-F | $OCH_3$ | H | $CH=CH_2$ | p-nitrobenzyl |
| 2-Cl | 7-$OCH_3$ | OH | $CH_3S$ | F | $CH_2CCl_3$ |
| 2-Br | H | $OCH_3$ | H | $CH_3$ | $Na^+$ |
| 4-Cl | 5-Cl | $OCH_3$ | H | $CH_3$ | $CH_3$ |
| 5-$NH_2$ | H | OH | H | Cl | $CH_2CH=CH_2$ |
| 5-$NHCOCH_3$ | H | $OCH_3$ | H | $OCH_3$ | $CH(Cl)_2$ |

-continued

Compounds of the formula

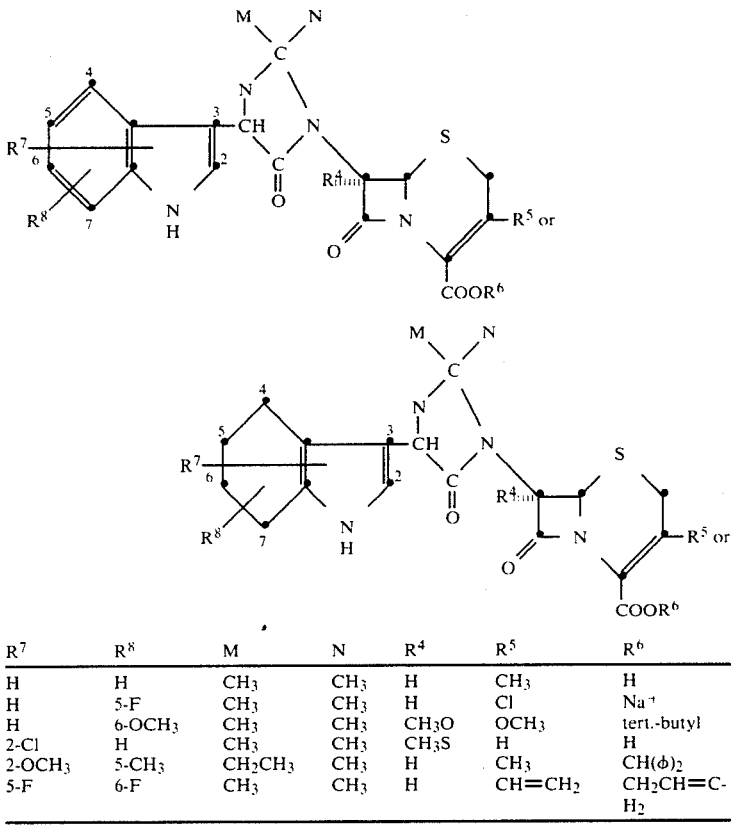

| R7 | R8 | M | N | R4 | R5 | R6 |
|---|---|---|---|---|---|---|
| H | H | CH3 | CH3 | H | CH3 | H |
| H | 5-F | CH3 | CH3 | H | Cl | Na+ |
| H | 6-OCH3 | CH3 | CH3 | H | CH3O | OCH3 | tert.-butyl |
| 2-Cl | H | CH3 | CH3 | CH3S | H | H |
| 2-OCH3 | 5-CH3 | CH2CH3 | CH3 | H | CH3 | CH(φ)2 |
| 5-F | 6-F | CH3 | CH3 | H | CH=CH2 | CH2CH=CH2 |

The synthesis of the compounds provided by this invention is further illustrated by the following preparations and working examples. The examples are illustrative only and are not intended to limit the invention in any respect.

PREPARATION 1

3-Indolylglycine

A solution of 144 g (1.2M) of indole in 1500 ml of diethyl ether and 113 ml of pyridine was added dropwise over ninety minutes to a cold (5° C.) stirred solution of 600 ml of diethyl ether containing 200 g of ethyl oxalyl chloride. The reaction mixture was warmed to ambient temperature and stirred for twenty-four hours, and then was diluted with 200 ml of water. The organic layer was separated, dried, and the solvent was removed by evaporation under reduced pressure to give 217 g of ethyl α-oxo-α-(3-indolyl)acetate.

The product thus obtained was combined with 92 g (1.3M) of hydroxylamine hydrochloride and 122 g (0.62M) of barium carbonate in 6 liters of methanol. The reaction mixture was heated at reflux for sixteen hours and then cooled to room temperature. The insolubles were removed by filtration and the filtrate was concentrated to dryness to provide a white solid. The white solid was dissolved in 500 ml of ethyl acetate, washed several times with water and dilute hydrochloric acid, and dried. Removal of the solvent afforded 118 g of ethyl α-hydroxyimino-α-(3-indolyl)-acetate.

A mixture of 5.8 g of the oxime thus prepared in 83 ml of methanol and 10 ml of tetrahydrofuran containing 1.2 g of 5% palladium on carbon was stirred at 24° C. under hydrogen at 60 psi for ten hours. The reaction mixture was filtered and the filtrate was concentrated to dryness to give an oil. The oil was dissolved in 50 ml of 1N hydrochloric acid and washed with diethyl ether. the aqueous acid layer was made alkaline with sodium bicarbonate and then extracted with ethyl acetate. The organic layer was washed with water, dried and the solvent was removed by evaporation to provide 2.5 g of ethyl 3-indolylglycine. Hydrolysis of 1.0 g of the ester thus formed by reaction with 1N sodium hydroxide afforded 0.73 g of 3-indolylglycine.

PREPARATION 2

N-tert.-Butoxycarbonyl 3-indolylglycine

To a stirred solution of 3 g (9.27 mM) of 3-indolylglycine in 30 ml of water and 30 ml of dioxane containing 1.75 g of sodium bicarbonate were added in one portion 2.63 g (12 mM) of di-tert.-butyldicarbonate. The reaction mixture was warmed to 60° C. and stirred for five hours, and then was cooled to 25° C. and stirred for an additional seventeen hours. The reaction mixture was concentrated in volume and the product was extracted into ethyl acetate. The organic layer was dried and the solvent was removed to give 2.13 g of N-tert.-butoxycarbonyl-3-indolylglycine.

NMR (DMSOd6): δ1.4 (s, 9H); δ5.29 (d, 1H); δ7.0–7.8 (m, 5H).

PREPARATION 3

D-(N-Chloroacetyl-3-indolyl)glycine

By following the procedure described in *Methods in Enzymology*, 44, 746 (1976), 66.3 g of D,L-(N-chloroacetyl-3-indolyl)glycine was chromatographed over a column packed with 20 g of N-acyl-L-amino acid amidohydrolase on 60 g of DEAE Sephadex solid support, eluting with 0.1M potassium hydrogen phosphate pH 7.08 buffer. Fractions shown by thin layer chromatographic analysis to contain the desired product were combined and the pH was adjusted to 2.0 by addition of 1N hydrochloric acid. The acid solution was extracted several times with ethyl acetate, and the extracts were combined, washed with water, dried, and the solvent was removed by evaporation under reduced pressure to afford 35 g of D-(N-chloroacetyl-3-indolyl)glycine.

EXAMPLE 1 tert.-Butyl D,L-7-(N-tert.-butoxycarbonyl-3-indolyl)glycylamido-3-methyl-3-cephem-4-carboxylate To a cold (0° C.) stirred solution of 1.16 g (8.58 mM) of 1-hydroxybenzotriazole in 20 ml of N,N-dimethylacetamide were added 1.26 ml (9.04 mM) of triethylamine and 0.68 ml (8.78 mM) of methanesulfonyl chloride. The reaction mixture was stirred at 0° C. for thirty minutes, warmed to 15° C., and then diluted by addition of 1.26 ml of triethylamine and 2.13 g (7.36 mM) of DL-N-tert.-butoxycarbonyl-3-indolylglycine. After stirring the reaction mixture for seventy minutes at 25° C., there were added in one portion 510 mg (1.88 mM) of tert.-butyl 7-amino-3-methyl-3-cephem-4-carboxylate. The reaction mixture was stirred at 25° C. for three hours, and then concentrated to dryness by evaporation of the solvent. The product was dissolved in 100 ml of ethyl acetate, washed several times with 1N hydrochloric acid, 5% aqueous sodium bicarbonate, and water, dried, and the solvent was removed by evaporation under reduced pressure to afford 5.3 g of tert.-butyl D,L-7-(N-tert.-butoxycarbonyl-3-indolyl)glycylamido-3-methyl-3-cephem-4-carboxylate.

NMR (CDCl$_3$): $\delta$1.5 (two singlets, 9H); $\delta$2.03 and 2.04 (two singlets, 3H); $\delta$2.9–3.55 (m, 2H); $\delta$4.9 (two doublets, 1H); $\delta$5.4–5.9 (m, 2H); $\delta$7.0–8.0 (m, 1H).

Four grams of the product thus produced was chromatographed twice over a silica gel column, eluting with a mixture of 2% by volume of ethanol, 15% by volume of ethyl acetate and 83% by volume of isooctane. Fractions containing the slower moving material were combined and concentrated to give an oil which was chromatographed again over silica gel, eluting with a gradient of hexane-ethyl acetate, starting with 100% hexane and finishing with 100% ethyl acetate. Fractions containing the product were combined and concentrated to dryness to give 650 mg of tert.-butyl D-7-(N-tert.-butoxycarbonyl-3-indolyl)glycylamido-3-methyl-3-cephem-4-carboxylate.

EXAMPLE 2

D-7-(3-Indolylglycylamido)-3-methyl-3-cephem-4-carboxylic acid trifluoroacetate To a cold (0° C.) stirred solution of 500 mg of tert.-butyl D-7-(N-tert.-butoxycarbonyl-3-indolyl)glycylamido-3-methyl-3-cephem-4-carboxylate (from Example 1) in 5 ml of dichloromethane containing 1 ml of triethylsilane was added dropwise over one minute 1 ml of trifluoroacetic acid. The reaction mixture was stirred for five minutes at 0° C. following the addition, and the solvents were then removed by evaporation under reduced pressure. The product was triturated with 5 ml of diethyl ether, dissolved in 5 ml of water, and lyophilized to provide 480 mg of D-7-(3-indolylglycylamido)-3-methyl-3-cephem-4-carboxylic acid trifluoroacetate.

NMR (D$_2$O): $\delta$1.68 (s, 3H); $\delta$3.05 (q, 2H); $\delta$4.92 (d, 1H); $\delta$5.51 (s, 1H); $\delta$5.61 (d, 1H); $\delta$7.1–7.7 (m, 5H).

EXAMPLE 3

Following the general procedure of Examples 1 and 2, DL-N-tert.-butoxycarbonyl-3-indolylglycine was reacted with tert.-butyl 7-amino-3-chloro-3-cephem-4-carboxylate to give, following chromatographic separation of the isomers and removal of the protecting groups, D-7-(3-indolylglycylamido)-3-chloro-3-cephem-4-carboxylic acid trifluoroacetate.

EXAMPLE 4

D-7-(3-Indolylglycylamido)-3-methoxy-3-cephem-4-carboxylic acid

A solution of 0.5 g (1.87 mM) of D-N-chloroacetyl-3-indolylglycine (from Preparation 3) in 5 ml of acetonitrile containing 0.51 g (2.06 mM) of N-ethoxycarbonyl-2-ethoxy-1,2-dihydroquinoline was stirred for five minutes and then added in one portion to a cold (0° C.) stirred solution of 2.36 g (11 mM) of 7-amino-3-methoxy-3-cephem-4-carboxylic acid in acetonitrile containing 12 ml of bis(trimethylsilyl)trifluoroacetamide. The reaction mixture was stirred at 0° C. for thirty minutes and then warmed to 25° C. and stirred for an additional two hours. The reaction mixture was added to water and the pH was adjusted to 2.0 by addition of 1N hydrochloric acid. The aqueous acid solution was extracted several times with ethyl acetate, and the extracts were combined and concentrated to dryness to give an oil. The oil was dissolved in dichloromethane and treated with excess diphenyldiazomethane to provide, following removal of the solvent, 0.7 g of diphenylmethyl 7-D-(N-chloroacetyl-3-indolyl)glycylamido-3-methoxy-3-cephem-4-carboxylate.

The product thus formed was dissolved in 30 ml of methanol containing 2.0 g of thiourea and the reaction mixture was stirred at 25° C. for one hour. The solution was added to 100 ml of water and the pH was adjusted to 2.0 by addition of 1N hydrochloric acid. The aqueous acid solution was extracted with ethyl acetate, and the ethyl acetate solution was dried and concentrated to dryness to give D-7-(3-indolylglycylamido)-3-methoxy-3-cephem-4-carboxylic acid.

EXAMPLE 5

D-7-(N-Chloroacetyl-3-indolyl)glycylamido-3-methyl-3-cephem-4-carboxylic acid A solution of 17.94 g (83.6 mM) of 7-amino-3-methyl-3-cephem-4-carboxylic acid in 190 ml of acetonitrile containing 22.8 ml (91.2 mM) of bis(trimethylsilyl)acetamide was stirred at 25° C. for twenty minutes. A portion of this solution (156 ml, 35.5 mM) was added dropwise over fifteen minutes to a cold (0° C.) stirred solution of 3.80 g (14.2 mM) of D-(N-chloroacetyl-3-indolyl)glycine (from Preparation 3) in 38 ml of acetonitrile containing 3.88 g (15.7 mM) of N-ethoxycarbonyl-2-ethoxy-1,2-dihydroquinoline. The reaction mixture was warmed to 25° C. following complete addition, and was stirred for sixty minutes. The reaction mixture was diluted by addition of 190 ml of ethyl acetate and washed two times with 190 ml portions of 1N hydrochloric acid, and once with 190 ml of brine. The organic layer was then extracted three times with 190 ml portions of 1M pH 7.0 buffer (1:1 v/v potassium hydrogen phosphate and potassium dihydrogen phosphate). The extracts were combined, acidified to pH 2.0 by addition of 12N hydrochloric acid, and extracted three times with fresh ethyl acetate. The extracts were combined, washed with brine, dried, and the solvent was removed by evaporation to give 4.96 g (68.6% yield) of D-7-(N-chloroacetyl-3-indolyl)glycylamido-3-methyl-3-cephem-4-carboxylic acid.

NMR (DMSOd$_6$): $\delta$1.93 (s, 3H), $\delta$3.31 (q, 2H); $\delta$4.10 (s, 2H); $\delta$4.95 (d, 1H); $\delta$5.62 (dd, 1H); $\delta$5.87 (d, 1H); $\delta$6.9–7.8 (m, 5H); $\delta$8.6 (d, 1H); $\delta$9.1 (d, 1H); $\delta$11.0 (broad s, 1H).

EXAMPLE 6

D-(3-Indolylglycylamido)-3-methyl-3-cephem-4-carboxylic acid

A solution of 5.2 g (11.2 mM) of D-7-(N-chloroacetyl-3-indolyl)glycylamido-3-methyl-3-cephem-4-carboxylic acid (prepared as described in Example 5) in 38 ml of acetone containing 9.4 ml of water and 1.88 g (24.7 mM) of thiourea was stirred at 25° C. for fifteen hours. The reaction mixture was added to 188 ml of water and stirred at 25° C. for an additional hour. The pH was then adjusted to 7.5 by addition of 1N sodium hydroxide, and the alkaline solution stood at 25° C. for three hours, maintaining the pH at 7.5 by periodic addition of sodium hydroxide. The reaction mixture was then lyophilized to provide D-7-(3-indolylglycylamido)-3-methyl-3-cephem-4-carboxylic acid.

The indolylglycyl cephalosporins provided by this invention are valuable antibiotic substances, or intermediates therefor. The compounds are particularly effective against a wide variety of gram-positive bacteria. The antibiotic compounds are thus useful for treating infections in animals caused by gram-positive bacteria. The compounds are particularly effective in the treatment of upper respiratory infections and similar diseases caused by H. influenza, S. aureus, S. pyogenes, and the like. The compounds are also effective in the treatment of diseases caused by anaerobic cocci such as *Peptostreptococcus anaerobius, Peptostrept. intermedius, Peptostrept. productus, Peptococcus osaccharolyticus, P. prevotii, P. avaerobius, Bacteroides fragilis, Propionibacterium acnes, Fusobacterium necrophorum*, and the like.

A typical and preferred compound provided by this invention is 7-(3-indolylglycylamido)-3-methyl-3-cephem-4-carboxylic acid, the compound illustrated in Example 2. The antibacterial activity of this compound and others of the invention has been determined in standard in vitro agar dilution assays against a variety of gram positive and gram negative microorganisms. The following Table presents typical minimum inhibitory concentrations (MIC's) in $\mu$g/ml for several compounds of the invention when evaluated against the indicated microorganisms. MIC's for several known compounds are also presented for comparison.

TABLE I

| | | Agar Dilution MIC ($\mu$g/ml) | | | | |
|---|---|---|---|---|---|---|
| | | Ampi- | Cepha- | Compound of | | |
| Organism | Strain | cillin | lexin | Ex. 2 | Ex. 3 | Ex. 4 |
| Staph. aureus | X1.1 | 0.125 | 2 | 4 | 4 | 4 |
| | V41 | 8 | 8 | 8 | 32 | 32 |
| | X400 | 128 | >128 | 64 | 64 | 64 |
| | S13E | 32 | 128 | 32 | 8 | 8 |
| Staph. epi | EPI1 | 16 | 32 | 16 | 16 | 16 |
| | EPI2 | 64 | 128 | 16 | 32 | 16 |
| Strep. A | C203 | 0.03 | 0.5 | 0.25 | 0.5 | 0.25 |
| Strep PN | PARK | 0.03 | 2 | 0.5 | 0.25 | 0.5 |
| Strep. D | X66 | 4 | 128 | 32 | 16 | 64 |
| | 9960 | 2 | 128 | 16 | 16 | 16 |
| E. coli | N10 | 8 | 8 | 32 | 16 | 16 |
| | EC14 | 4 | 4 | 32 | 8 | 8 |
| | TEM | 32 | 4 | 16 | 16 | 32 |
| Klebsiella | X26 | 16 | 2 | 16 | 4 | 16 |
| | KAE | 128 | 128 | >128 | >128 | >128 |
| | X68 | 16 | 8 | 128 | 16 | 16 |
| Shig. sonn. | N9 | 4 | 8 | 32 | 32 | 32 |
| Enterobacter | X68 | 8 | 0.03 | 32 | >128 | >128 |
| | C32 | >128 | 0.125 | >128 | >128 | >128 |
| | EB17 | 128 | 0.06 | >128 | >128 | >128 |
| Salmonella | X514 | 1 | 0.6 | 32 | 16 | 16 |
| | 1335 | 4 | 0.25 | 128 | 16 | 32 |

The data in the above Tables clearly demonstrate the potent antibacterial activity possessed by the compounds of this invention.

In addition to possessing potent antibacterial activity against a wide variety of microorganisms, particularly gram positive organisms and anaerobes, the compounds of this invention also have demonstrated very favorable pharmacokinetics in animals. For example, when 7-(3-indolylglycylamido)-3-methyl-3-cephem-4-carboxylic acid was administered to rats at an intravenous dose of 20 mg/kg, the plasma concentration after one hour was 15.0 $\mu$g/ml, and after four hours, 6.0 $\mu$g/ml. About 60% of the above compound was recovered in the urine of rats following a 20 mg/kg subcutaneous dose. Less than 5% was recovered from the bile.

The favorable pharmacokinetics of the compounds provided by this invention, coupled with their excellent oral gram positive antibacterial activity and their good stability to $\beta$-lactamases, make them particularly attractive agents for the treatment of a number of diseases of bacterial origin. The compounds are especially well suited for the treatment of outpatients, and especially for subjects suffering from mild upper respiratory infections.

The treatment of animals suffering from bacterial diseases, or suspected of developing a bacterial infection, is thus another embodiment of this invention. The antibacterial method of treatment provided by this invention will be practiced by administering an antibacterially effective amount of a indolylglycyl cephalosporin antibiotic as defined herein to an animal in need of treatment. The method can be practiced therapeutically or prophlactically. The amount of active antibiotic to be administered according to the method will vary depending upon the particular compound selected for use, the severity of the disease being treated or guarded against, the individual undergoing treatment, and related factors commonly encountered with such treatments. Normally, however, the compounds will be administered at a dose of about 0.5 to about 50 mg/kg of animal body weight, and more preferably at a rate of about 1 to about 10 mg/kg. Such amounts will be administered once or twice each day, or more often as needed to treat the particular disease or subject undergoing treatment according to the present method. A typical daily dose for an average adult human will be about 200 to about 500 mg per day.

The antibiotic compounds provided by this invention are active by both the oral and parenteral routes of administration, and accordingly can be formulated for any such desired route of administration. Such formulations constitute yet another embodiment of this invention. The formulations of this invention will comprise from about 0.1 to about 95 percent by weight of an active indolylglycyl cephalosporin antibiotic of the invention, admixed with a pharmaceutically acceptable carrier, diluent or excipient therefor. Typical formulations will contain from about 10 to about 60 percent by weight of active ingredient, and more preferably about 20 to about 50 percent.

For convenient oral administration, the compounds can be admixed with any of a number of diluents, excipients and carriers commonly employed in oral formulations, and molded into tablets, pills, troches, or encapsulated into gelatin capsules. Typical carriers, diluents and excipients commonly employed include potato starch, corn starch, sucrose, dextrose, microcrystalline cellulose, dicalcium phosphate, alginic acid, acacia; lubricants such as magnesium stearate; binders such as gum tragacanth or gelatin; and flavoring agents such as peppermint oil, cherry or strawberry flavoring, oil of wintergreen, and the like. The compounds can also be formulated as syrups or elixirs employing common diluents such as a fatty oil, methyl or propyl parabens, suitable dyes and flavoring agents. The compounds can also be formulated in the form of a buccal seal, logenze or other suitable device for sustained controlled delivery of the active ingredient over a prolonged period.

The antibiotics of the invention can also be formulated for parenteral administration, for example via the intravenous, intramuscular or subcutaneous routes, as well as the transdermal route. Such compositions normally will contain from about 0.1 to about 20.0 percent by weight of active ingredient. Typical excipients, diluents and carriers for parenteral formulations include isotonic saline, dilute aqueous dextrose, the polyhydric aliphatic alcohols or mixtures thereof, for instance glycerin, propylene glycol, polyethylene glycol, and the like. Parenteral solutions may also contain preservatives such as phenethylalcohol, methyl and propyl parabens, thimerosal and the like. If needed, about 0.05 to about 0.20 percent by weight of an antioxidant such as sodium metabisulfite or sodium bisulfite can also be employed. For intravenous use, preferred formulations will employ an initial concentration down to about 0.05 to about 0.25 mg/ml of active ingredient, and for intramuscular injection, a preferred concentration of active ingredient is about 0.25 to about 0.50 mg/ml.

Examples of typical pharmaceutical formulations contemplated by this invention include the following.

EXAMPLE 7

Formulation of Oral Suspension

| Ingredient | Amount |
| --- | --- |
| Sodium D-7-(3-indolylglycylamido)-3-methyl-3-cephem-4-carboxylate | 500 mg |
| Sorbitol solution (70% N.F.) | 40 ml |
| Sodium benzoate | 150 mg |
| Saccharin | 10 mg |
| Cherry flavor | 50 mg |

-continued

| Ingredient | Amount |
| --- | --- |
| Distilled water q s ad | 100 ml |

The sorbitol solution is added to 40 ml of distilled water and the indolylglycyl cephalosporin is suspended thereon. The saccharin, sodium benzoate, and flavoring are added and dissolved. The volume is adjusted to 100 ml with distilled water. Each ml of syrup contains 5 mg of the indolylglycyl cephalosporin antibiotic. This oral formulation is ideally suited for pediatric use.

EXAMPLE 8

Preparation of 250 mg capsule

| Ingredient | Amount |
| --- | --- |
| 7-[6-Chloro-3-(4,5,6,7-tetrahydro-indolyl)glycylamido]-3-methyl-3-cephem-4-carboxylic acid | 250 mg |
| Lactose | 150 mg |
| Corn starch | 100 mg |
| | 500 mg |

The ingredients are blended to uniformity and encapsulated into gelatin capsules. Such capsules are orally administered at the rate of about one or two each day for the treatment of upper respiratory bacterial infections, including pharyngitis and tonsillitis.

EXAMPLE 9

Preparation of Parenteral Solution

In a solution of 700 ml of propylene glycol and 200 ml of distilled water for injection is dissolved 20.0 grams of D-7-(3-indolylglycylamido)-3-methoxymethyl-3-cephem-4-carboxylic acid, hydrochloride. The pH of the solution is adjusted to 5.5 with hydrochloric acid, and the volume is made up to 1000 ml with distilled water. The formulation is sterilized, filled into 5.0 ml ampoules each containing 2.0 ml (representing 40 mg of active ingredient) and sealed under nitrogen.

We claim:

1. A compound of the formula

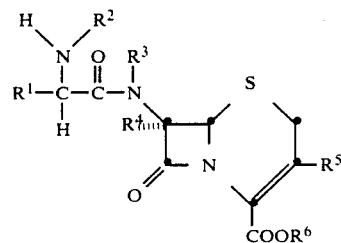

wherein: $R^1$ is

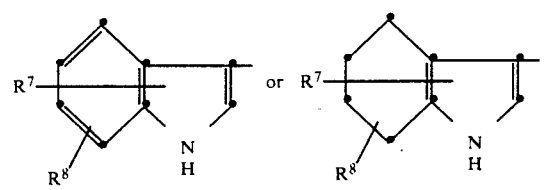

in which $R^7$ and $R^8$ independently are hydrogen, halo, hydroxy, $C_1-C_4$ alkyl, $C_1-C_4$ alkoxy, nitro, amino, $C_1-C_4$ alkanoylamino, $C_1-C_4$ alkylsulfonylamino, or when $R^7$ and $R^8$ are on adjacent carbon atoms, they may be taken together to form methylenedioxy;

$R^2$ is hydrogen, an amino protecting group, and $R^3$ is hydrogen, or $R^2$ and $R^3$ taken together are

where
M and N independently are $C_1-C_4$ alkyl;
$R^4$ is hydrogen, methoxy or methylthio;
$R^5$ is hydrogen, methoxy, methyl, halo, methoxymethyl, or vinyl;
$R^6$ is hydrogen, a salt forming cation group, or a carboxy protecting group; and the pharmaceutically acceptable acid addition salts thereof.

2. The compound of claim 1 wherein $R^2$ and $R^3$ are taken together to form

3. The compound of claim 1 wherein $R^1$ is

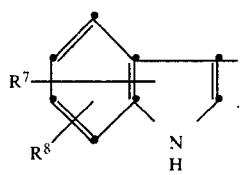

4. The compound of claim 3 wherein $R^7$ is hydrogen or halo.
5. The compound of claim 4 wherein $R^7$ is hydrogen.
6. The compound of claim 5 wherein $R^4$ is hydrogen.
7. The compound of claim 6 wherein $R^5$ is methyl or chloro.
8. The compound of claim 7 wherein $R^6$ is hydrogen or a salt forming cation.
9. The compound of claim 8, said compound being D-7-(3-indolyl)glycylamido-3-methyl-3-cephem-4-carboxylic acid.
10. The compound of claim 8 wherein $R^8$ is halo.
11. The compound of claim 10 wherein $R^8$ is chloro.
12. The compound of claim 10 wherein $R^8$ is fluoro.
13. The compound of claim 8 wherein $R^8$ is hydroxy.
14. The compound of claim 8 wherein $R^8$ is $C_1-C_4$ alkoxy.
15. The compound of claim 8 wherein $R^8$ is amino.
16. The compound of claim 6 wherein $R^5$ is hydrogen.
17. The compound of claim 6 wherein $R^5$ is methoxymethyl.
18. The compound of claim 6 wherein $R^5$ is vinyl.
19. The compound of claim 1 wherein $R^1$ is

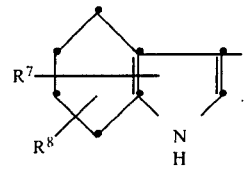

20. The compound of claim 19 wherein $R^7$ is hydrogen.
21. The compound of claim 20 wherein $R^4$ is hydrogen.
22. The compound of claim 21 wherein $R^5$ is methyl or chloro.
23. The compound of claim 22 wherein $R^6$ is hydrogen or a salt forming cation.
24. A method of treating bacterial infections in animals comprising administering an effective amount of an antibacterial compound of claim 1.
25. The method of claim 24 employing a compound wherein $R^2$, $R^3$ and $R^4$ all are hydrogen.
26. The method of claim 25 employing a compound wherein $R^6$ is hydrogen or a salt forming cation.
27. The method of claim 26 employing a compound wherein $R^5$ is methyl or chloro.
28. The method of claim 27 employing a compound wherein $R^1$ is

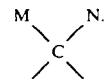

29. The method of claim 28 employing a compound wherein $R^7$ is hydrogen.
30. The method of claim 29 employing D-7-(3-indolyl)glycylamido-3-methyl-3-cephem-4-carboxylic acid.
31. The method of claim 29 employing a compound wherein $R^8$ is fluoro.
32. The method of claim 29 employing a compound wherein $R^8$ is chloro.
33. A pharmaceutical formulation useful for treating bacterial infections comprising an antibacterially effective amount of a compound of claim 1 admixed with a pharmaceutical carrier, diluent or excipient.
34. The formulation of claim 33 employing a compound wherein $R^2$, $R^3$ and $R^4$ all are hydrogen.
35. The formulation of claim 34 employing a compound wherein $R^6$ is hydrogen or a salt forming cation.
36. The formulation of claim 35 employing a compound wherein $R^5$ is methyl or chloro.
37. The formulation of claim 36 employing a compound wherein $R^1$ is

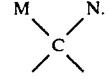

38. The formulation of claim 37 employing a compound wherein $R^7$ is hydrogen.
39. The formulation of claim 38 employing a compound wherein $R^8$ is hydrogen.
40. The formulation of claim 38 employing a compound wherein $R^8$ is halo.

* * * * *